United States Patent

Wissmann et al.

[11] Patent Number: 4,814,484
[45] Date of Patent: Mar. 21, 1989

[54] THYRONINE DERIVATIVES

[75] Inventors: Hans Wissmann, Bad Soden am Taunus, Fed. Rep. of Germany; Henning Hachmann, Lexington, Mass.; Guido Simons, Ingelheim am Rhein; Helmut Strecker, Pfungstadt, both of Fed. Rep. of Germany

[73] Assignee: Hoechst Aktiengesellschaft, Frankfurt am Main, Fed. Rep. of Germany

[21] Appl. No.: 1,207

[22] Filed: Jan. 7, 1987

[30] Foreign Application Priority Data

Jan. 9, 1986 [DE] Fed. Rep. of Germany ....... 3600365

[51] Int. Cl.⁴ ............................................. C07C 101/30
[52] U.S. Cl. ................................ 560/39; 260/502.5 D
[58] Field of Search ............................ 424/1.1; 560/39; 260/502.5 D

[56] References Cited

PUBLICATIONS

Chemical Abstracts, vol. 107, No. 21:198924y.
Chemical Abstracts, vol. 109, No. 11:89357m.

Primary Examiner—Robert J. Warden
Assistant Examiner—Stephen C. Wieder
Attorney, Agent, or Firm—Finnegan, Henderson, Farabow, Garrett, & Dunner

[57] ABSTRACT

The invention relates to new thyronine derivatives of the formula

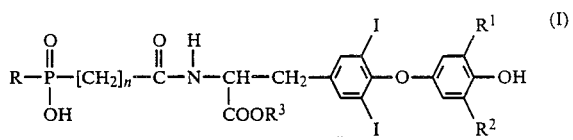

in which n is 1–6, R denotes hydroxyl, alkyl or aryl, $R^1$ and $R^2$ are identical or different and denote iodine or hydrogen, and $R^3$ denotes hydrogen, alkyl or aralkyl, a process for the preparation thereof, and the use thereof for carrying out radioimmunoassays.

4 Claims, No Drawings

THYRONINE DERIVATIVES

The invention relates to novel thyronine derivatives of the general formula I,

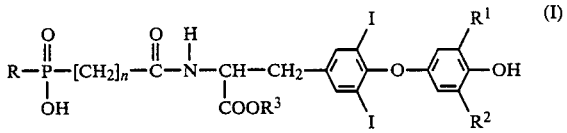

in which
n represents an integer between 1 and 6,
R denotes hydroxyl, ($C_1$–$C_6$)-alkyl or ($C_6$–$C_{10}$)-aryl,
$R^1$ and $R^2$ are identical or different and denote iodine or hydrogen, and
$R^3$ denotes hydrogen ($C_1$–$C_6$)-alkyl or ($C_7$–$C_{10}$)-aralkyl, and also the salts thereof.

Preferred compounds of the formula I are those in which $R^1$ and $R^2$ are as defined above and n is 1 to 4, R denotes hydroxyl or ($C_1$–$C_4$)-alkyl and $R^3$ denotes hydrogen or ($C_1$–$C_4$)-alkyl, particularly hydrogen, methyl or ethyl.

Alkyl may be straight-chain or branched. ($C_7$–$C_{10}$)-aralkyl is taken to mean, for example, benzyl or phenethyl, preferably benzyl. ($C_6$–$C_{10}$)-aryl preferably denotes phenyl. Salts of the compounds of the formula I are taken to mean, in particular, alkali metal salts, alkaline earth metal salts and ammonium salts.

The invention furthermore relates to a process for the preparation of compounds of the formula I which comprises reacting compounds of the formula II,

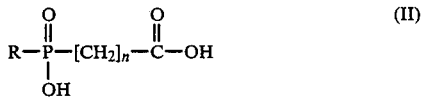

in which R and n are as defined above, or an activated derivative thereof, with compounds of the formula III,

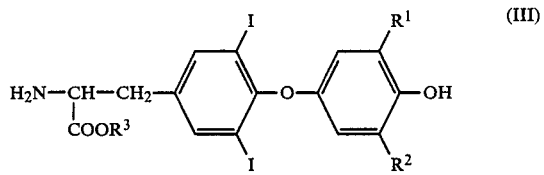

in which $R^1$, $R^2$ and $R^3$ are as defined above and $R^3$ is preferably H, or employing esters of the formula III ($R^3 \neq H$) converting the resultant esters of the formula I ($R^3 \neq H$), if appropriate, into the free acid of the formula I ($R^3 = H$), and converting the compounds of the formula I thus obtained, if appropriate, into the salts thereof.

All current peptide synthesis methods, such as, for example, the carbodiimide method (see, for example, Schröder and Lübke, the Peptides, Volume I, Academic Press New York, London 1963, pages 108–111), the mixed anhydrides method (see, for example, ibidem, pages 77–97) and also the methods using alkylphosphonic anhydrides or dialkylphosphinic anhydrides (Kleiner and Wissmann, Angew. Chem. 92 [1980] 129 or EP-A-56 618), may be used as methods for the formation of the amide bond between the thyronine esters of the formula III and the phosphino- or phosphonoalkane-carboxylic acids of the formula II.

The compound having a free carboxyl group may be liberated from the esters of the formula I in a fashion which is known per se by hydrolysis or hydrogenolysis. The saponification of the lower alkyl esters using mixed aqueous alkalis is preferred.

The compounds according to the invention are distinguished by specific solubility, adsorption and bonding properties which are favorable for radioimmunoassay of thryonine derivatives.

Compounds of the formula I may be radioactively labelled in a conventional fashion (for example by iodine exchange or iodination). The labelling with the $^{125}I$ isotope is preferred.

The following examples describe the present invention without limiting it.

(1) Methylphosphinoacetyltetraiodothyronine 160 mg (1.16 millimoles) of methylphosphinoacetic acid and 0.4 ml (3.16 millimoles) of N-ethylmorpholene are dissolved in a mixture of 2.5 ml of dimethylformamide and 2.5 ml of methanephosphonic bisdimethylamide. 0.4 ml (2.32 millimoles) of methylethylphosphinic anhydride are then added dropwise with ice cooling. The mixture is then stirred for 10 minutes at room temperature and 800 mg (1.03 millimoles) of thyroxine (tetraiodothyronine) are subsequently added. The reaction solution is left to stand overnight at room temperature, and the reaction product is then precipitated by addition of water and acidification to pH 3 using dilute aqueous HCl. Yield of crude product: 920 mg.

Thin layer chromatography (TLC) of the product (silica gel 60, (Merck), solvent $CHCl_3/CH_3OH$/glacial acetic acid, 100:20:2) shows that the tetraiodothyronine starting material is completely reacted. The crude product is purified over a silica gel 60 column (4.5×35 cm) using the solvent system n-butanol/3.3% strength $NH_4OH/CH_3OH$ (100:20:2). The purified product, produced as a lightly-colored amorphous powder, displays an $R_f$ value of 0.75 in the abovementioned chloroform system. The $^1H$ NMR spectrum shows the expected characteristics.

(2) Methylphosphinopropionyltriiodothyronine methyl ester 360 mg (0.52 millimole) of triiodothyronine methyl ester hydrochloride and 220 mg (1.07 millimoles) of dicyclohexylcarbodiimide, dissolved in 0.5 ml of dimethylformamide, are added successively to the solution of 110 mg of methylphosphinopropionic acid (0.72 millimole) and 0.3 ml (2.35 millimoles) of N-ethylmorpholine in 2 ml of dimethylformamide with stirring, ice cooling and exclusion of moisture. The mixture is allowed to warm to room temperature with stirring, and the precipitated dicyclohexylurea is then filtered off under suction after standing for 28 hours under the exclusion of light at room temperature. The residue which remains after distilling off the solvent is precipitated repeatedly from ethanol/ether.

Yield of crude product: 365 mg.

(3) Methylphosphinopropionyltriidothyronine 348 mg of the crude product from example (2) are dissolved in 3 ml of methanol and the solution is stirred, after addition of 2N aqueous sodium hydroxide solution, for 4 hours at pH 12.5 whilst maintaining the pH using the hydroxide solution. The methanol is subsequently evaporated in vacuo from the reaction mixture, neutralized using dilute aqueous hydrochloric acid, the residue is taken up in water, and the suspension is acidified to pH 2.5 with stirring using 2N aqueous HCl. The precipitate is filtered off under suction, washed with water and dried over phosphorus pentoxide in vacuo.

Yield: 205 mg.

The product is characterized as such by elemental analysis and $^1$H NMR, and silica gel thin layer chromatography in several systems shows the absence of the starting materials.

(4) Phosphonoacetyldiiodothyronine

The preparation is carried out as described in example (2). After saponification, the product is purified by column chromatography on silica gel in the $CHCl_3/CH_3OH/H_2O$/glacial acetic acid, 100:45:6:1.5, system, and identified by $^1$H NMR spectroscopy.

(5) Methylphosphinoacetyldiiodothyronine

The compound was prepared analogously to the procedure described in examples (2) and (3). Methylphosphinoacetic acid was used in place of methylphosphinopropionic acid and diiodothyronine methyl ester hydrochloride was used in place of triiodothyronine methyl ester hydrochloride. The final product was purified by inverse phase column chromatography on silica gel RP 18 using 75% strength methanol as eluent. The unary substance of the main fraction, differing in the TLC from the starting materials, was identified by mass spectrometry as the title compound.

We claim:

1. A compound of the formula I,

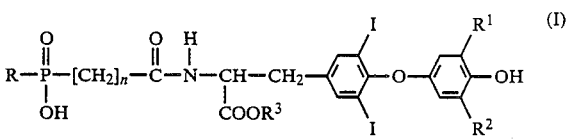

in which n represents an integer between 1 and 6,

R denotes hydroxyl, $(C_1-C_6)$-alkyl or $(C_6-C_{10})$-aryl, $R^1$ and $R^2$ are identical or different and denote iodine or hydrogen, and $R^3$ denotes hydrogen, $(C_1-C_6)$-alkyl or $(C_7-C_{10})$-aralkyl, and the salts thereof.

2. A compound of the formula I as claimed in claim 1, in which n is 1 to 4,

R denotes hydroxyl or $(C_1-C_4)$-alkyl, and $R^3$ denotes hydrogen or $(C_1-C_4)$-alkyl.

3. A compound of the formula I as claimed in claim 1, in which $R^3$ denotes hydrogen, methyl or ethyl.

4. A compound of the formula I as claimed in claim 1, in which at least one of the iodine atoms is radioactively labeled as $^{125}$I.

* * * * *